US005630430A

United States Patent [19]
Shultz et al.

[11] Patent Number: 5,630,430
[45] Date of Patent: *May 20, 1997

[54] WOUND CLOSURE DEVICE

[75] Inventors: Tod H. Shultz, Arlington; Cubie E. Ward, Jr., Grand Prairie, both of Tex.

[73] Assignee: Tecnol Medical Products, Inc., Fort Worth, Tex.

[*] Notice: The term of this patent shall not extend beyond the expiration date of Pat. No. 5,497,788.

[21] Appl. No.: 544,146

[22] Filed: Oct. 17, 1995

Related U.S. Application Data

[63] Continuation-in-part of Ser. No. 278,575, Jul. 20, 1994, Pat. No. 5,497,788, which is a continuation of Ser. No. 92,594, Jul. 16, 1993, abandoned.

[51] Int. Cl.$^6$ ...................................................... A61F 13/00
[52] U.S. Cl. ................................ 128/888; 602/42; 602/43; 602/54
[58] Field of Search ......................... 128/846, 888, 128/889; 602/41, 42, 43, 54

[56] References Cited

U.S. PATENT DOCUMENTS

| | | | |
|---|---|---|---|
| 1,644,508 | 10/1927 | Blake | 602/41 |
| 3,645,835 | 2/1972 | Hodgson | 161/146 |
| 3,918,446 | 11/1975 | Buttaravoli | 128/133 |
| 4,096,863 | 6/1978 | Kaplan et al. | 128/349 |
| 4,165,748 | 8/1979 | Johnson | 128/348 |
| 4,275,721 | 6/1981 | Olson | 128/133 |
| 4,583,976 | 4/1986 | Ferguson | 604/174 |
| 4,614,183 | 9/1986 | McCracken et al. | 128/132 |
| 4,678,462 | 7/1987 | Vaillancourt | 604/180 |
| 4,704,177 | 11/1987 | Vaillancourt | 156/226 |
| 4,838,868 | 6/1989 | Forgar et al. | 604/180 |
| 4,875,896 | 10/1989 | Kurtz | 604/187 |
| 4,898,587 | 2/1990 | Mera | 604/174 |
| 5,116,324 | 5/1992 | Brierley et al. | 604/180 |
| 5,160,328 | 11/1992 | Cartmell | 602/41 |
| 5,170,781 | 12/1992 | Loomis | 128/118 |
| 5,282,791 | 2/1994 | Lipton et al. | 604/180 |
| 5,336,162 | 8/1994 | Ota | 602/41 |
| 5,497,788 | 3/1996 | Inman | 602/43 |

OTHER PUBLICATIONS

"Steri-Strip™ Wound Closure System" Surgical Division, 3M HealthCare, ©1992 3M (3 pages).
"Alexander's Care of the Patient in Surgery" M Mosby, ©1995 Mosby-Year Book, Inc. (4 pages).
USSN 08/278,575 filed Jul. 20, 1994 "Wound Closure Device for Viewing a Wound and Method" — pending.
USSN 08/092,594 filed Jul. 16, 1993 "Wound Closure Device for Viewing a Wound and Method" — abandoned.
Patent Application USSN 29/045,913 filed Nov. 2, 1995 "Wound Closure with Multiple Adhesive Strips and Integral Cover Dressing" — pending.

*Primary Examiner*—Michael A. Brown
*Attorney, Agent, or Firm*—Baker & Botts, L.L.P.

[57] ABSTRACT

A closure device for use in closing lacerations, incisions, wounds and the like. The closure device includes a relatively narrow closure member connected at one end to an enlarged viewing member. Both members have adhesive layers applied in appropriate places to adhere the closure device to the patient. Protective members are arranged to cover the device so that the device can be handled and applied by a person wearing surgical gloves.

18 Claims, 3 Drawing Sheets

WOUND CLOSURE DEVICE

RELATED APPLICATIONS

This application is a continuation-in-part of application Ser. No. 08/278,575 filed Jul. 20, 1994, now U.S. Pat. No. 5,497,788, which is a continuation of application Ser. No. 08/092,594 filed Jul. 16, 1993, abandoned.

TECHNICAL FIELD OF THE INVENTION

This invention relates generally to devices for closing wounds, incisions, and lacerations. More particularly, but not by way of limitation, this invention relates to an improved adhesive device for closing wounds, incisions, and lacerations that can be easily applied by a person wearing surgical gloves and the like.

BACKGROUND OF THE INVENTION

The use of adhesive transparent film dressings and the use of adhesive closure strips is well known for the purpose of closing wounds. Usually, such wounds are relatively small or are located in a position where there is little or no distension of the skin as a result of movement by the injured person. Wounds, incisions, lacerations, and any related skin traumas wherein there is a separation of the skin are interchangeable terms as used herein.

An example of a transparent film dressing is given by Robert W. McCracken, et al., in U.S. Pat. No. 4,614,183, issued on Sep. 30, 1986. The device is often difficult to apply when the user is wearing surgical gloves.

Another example of a transparent film dressing, which also includes a wound closure feature is embodied in a device sold under the trade name "Steri-Strip", Laparoscopic Wound Closure System featuring "Tegaderm" Transparent Dressing and made by the Medical-Surgical Division of 3M Health Care, and related to U.S. Pat. No. 3,645,835. When using this dressing, it appears that a narrow closure member is removed, or partially removed, from a release treated paper backing and applied to close the wound. It is then necessary to remove a very thin transparent film that is separate from the closure member and apply this film to cover the area of the trauma. While this device may effectively close the wound, it is often difficult to apply when wearing gloves.

SUMMARY OF THE INVENTION

In accordance with the present invention, an improved wound closure device is provided to substantially reduce or eliminate shortcomings previously associated with such wound closure devices. One aspect of the present invention includes a closure device having a closure strip with an integral cover or dressing which allows viewing the wound during application of the closure device.

An object of the invention is to provide an integral thin film surgical dressing and closure strip that is easy to apply even when wearing surgical gloves and is effective to close a wound while providing a transparent cover for the wound after closure of the wound is accomplished.

A wound closure device constructed in accordance with the present invention includes an elongated closure member; an adhesive on a side of the closure member arranged to be located adjacent to the laceration; an enlarged, substantially transparent, viewing member having one end attached to an adjacent end of the closure member; and an adhesive on a side of the viewing member remote from the closure member for securing the viewing member to the skin adjacent to the laceration when the viewing member is disposed in overlying relation to the closure member.

As previously noted, the terms "wound", "incision", "laceration" and any similar or related trauma resulting in separation of the skin are interchangeable with respect to each other for purposes of defining and claiming the present invention.

BRIEF DESCRIPTION OF THE DRAWINGS

For a more complete understanding of the present invention, and the advantages thereof, reference is now made to the following written description taken in conjunction with the accompanying drawings in which like reference numbers indicate like features, and wherein.

DETAILED DESCRIPTION OF EXEMPLARY EMBODIMENTS

Figure 1:
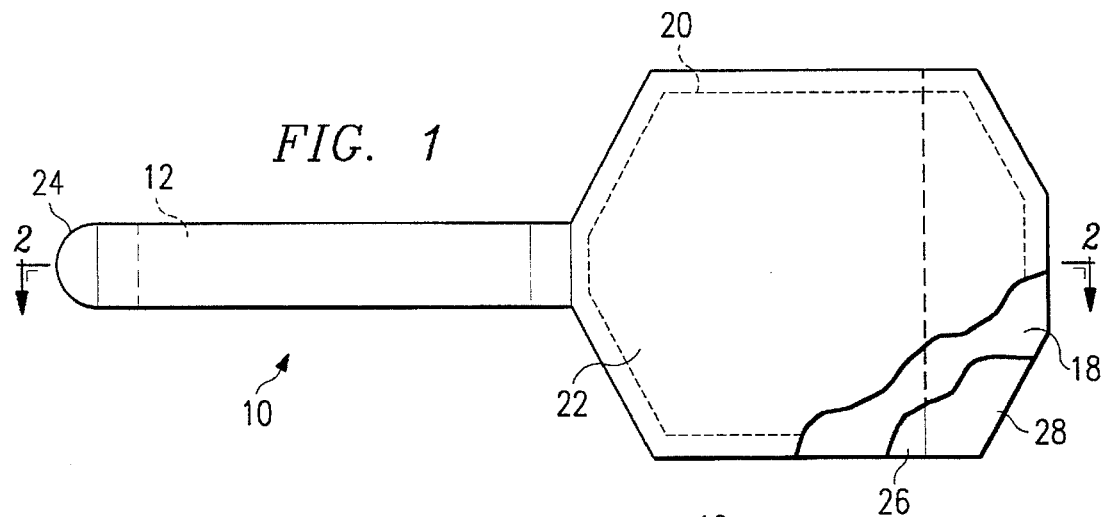
FIG. 1 is a plan view of an incision closure device constructed in accordance with the teachings of the present invention.

The preferred embodiments of the present invention and its advantages are best understood by referring to FIGS. 1–10 of the drawings, like numerals being used for like and corresponding parts of the various drawings.

It will be understood that the thicknesses of the layers of materials and other dimensions in the drawing have been greatly exaggerated for purposes of illustration. Further, directions, such as top and bottom refer to the location of the various members in the drawing and, in general, also to their positions relative to a patient. "Top" refers to a location remote from the patient, while "bottom" refers to a location adjacent to the patient.

Figure 2:
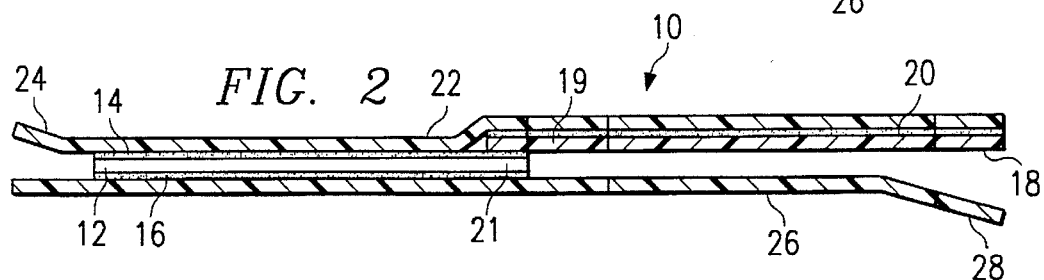
FIG. 2 is a cross-sectional view of the incision closure device of FIG. 1 taken generally along the line 2—2 of FIG. 1.

Referring to the drawing and to FIGS. 1 and 2 in particular, shown therein and generally designated by the reference character 10, is an incision closure device. The incision closure device 10 includes an elongated closure member 12 having top and bottom adhesive layers 14 and 16 thereon. The closure member is sometimes referred to as a suture strip. The bottom layer of adhesive 16, that is, the layer that will be disposed adjacent to the patient (See FIGS.

3 and 6), must be one that will cause the closure member 12 to adhere to the patient. For some applications, the closure member 12 may be constructed from a material that is transparent or at least translucent so that an incision or wound 17 can be viewed through the closure member 12 during application of the closure device 10 to the patient. For many applications, the closure member 12 is preferably formed from opaque material.

It should also be noted that the closure member is relatively narrow as compared to the length of the wound 17 (See FIGS. 4, 5, and 7) Usually, the closure member 12 will be substantially more narrow than the width of the wound 17 so that the wound can be viewed reasonably well even if the wound 17 cannot be seen through the member 12.

The closure device 10 also includes a viewing member 18 that is constructed from a transparent material such as polyurethane film. The viewing member 18 has one end 19 adhered to one end 21 of the closure member 12 forming a single member. An adhesive layer 20 is disposed on the top surface of the viewing member 18 for purposes that will become more apparent as the description proceeds. Preferably, the adhesive layer 20 completely covers the top surface of viewing member 18. Alternatively, adhesive layer 20 may be located in a relatively narrow band around the periphery of the viewing member 18 as shown in dash lines in FIG. 1 rather than fully coating the member 18.

The viewing member 18 is enlarged as compared to the closure member 12. It has a length that is about equal to that of the member 12, but has a width that is substantially larger than the width of the member 12. Preferably, the width of the viewing member 18 is not less than twice the width of the closure member 12. Manifestly, the object of having the large width is to cover the wound 17. If the wound 17 is very long it will most likely be sutured and the closure device 10 not used. However, closure devices 10 can be used by spacing several of them along the length of the wound. In any event, the width of the viewing member 18 is preferably not less than twice the width of the closure member 12.

The top protective member 22 and the viewing member 18 have been partially cut away so that the various superimposed members can be better shown in FIG. 1.

A first or top protective member 22 is located on top of the closure member 12 and on top of the viewing member 18 and is releasably attached thereto by the adhesive layers 14 and 20. A release coating is applied to the side of the member 22 adjacent to the adhesive layers 14 and 20 so the member 22 can be easily separated from the members 12 and 18 despite the presence of the adhesive layers 14 and 20.

The top protective member 22 is substantially coextensive with the members 12 and 18. However, to enable the member 22 to be easily removed even by a person wearing surgical gloves, the member 22 has a tab portion or end 24 that extends slightly past the closure member 12. The end 24 may be bent or turned slightly upwardly away from the patient to which the device 10 is being applied further facilitating the grasping of the end 24 by a person wearing gloves.

A second or bottom protective member 26 is located below the closure member 12 and below the viewing member 18 and is releasably attached thereto by the adhesive layer 16. The member 26 is not attached to the viewing member 18 since no adhesive is present on the bottom side of the viewing member 18. A release coating is applied to the side of the member 26 adjacent to the adhesive layer 16 so the member 26 can be easily separated from the member 12 despite the presence of the adhesive layer 16. End 24 of top protective member 22 may also be bent or otherwise offset from member 26 to further facilitate grasping end 24 by a person wearing gloves. For some applications, it may not be necessary to "bend" end 24.

The bottom protective member 26 is substantially coextensive with the members 12 and 18 and with the top protective member 22. However, to enable the member 26 to be easily removed even by a person wearing surgical gloves, the member 26 has a tab portion or end 28 adjacent to the lower side of the viewing member 18 that may be bent or turned slightly outwardly from the viewing member 18 to offset member 28 from viewing member 18 to further facilitate the grasping of the end 28 by a person wearing gloves. Other techniques in addition to bending may be satisfactorily used to offset member 28 from viewing member 18.

Both of the protective members 22 and 26 may be constructed from materials such as paper, polyester, polypropylene, and polyethylene. It is preferred that the top protective layer 22 be constructed from a material that is transparent which permits a full view of the wound 17 when using the device 10 to close the wound.

When the closure device 10 is removed from a sterile package (not shown), the device 10 is configured as described in detail hereinbefore and as shown in FIGS. 1 and 2. The bottom protective member 26 is removed by grasping the offset end or tab portion 28 and pulling the member 26 away from the remainder of the device 10. The offset end 28 enables a user wearing gloves to easily grasp and remove the member 26 which is coated with a release coating as previously described. The bottom protective member 26 is then discarded leaving the device 10 in the configuration shown in FIG. 3.

Figure 3:
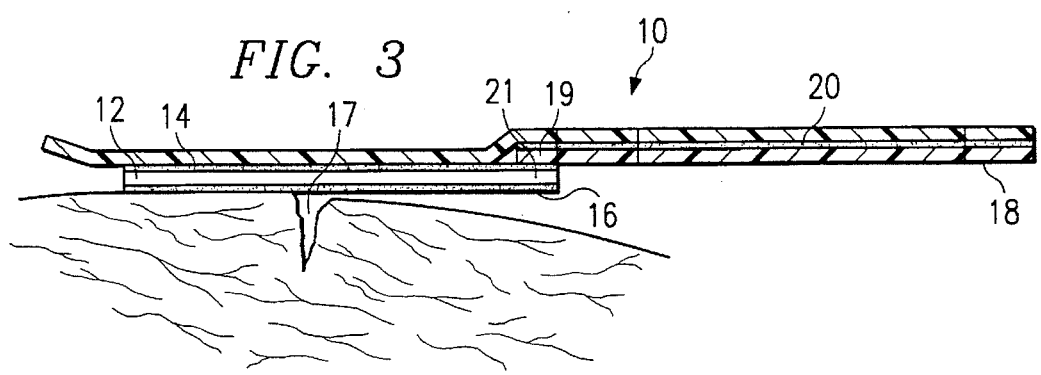
FIG. 3 is a cross-sectional view of the incision closure device of FIG. 1 positioned adjacent to an incision with a bottom protective member removed.
Figure 4:
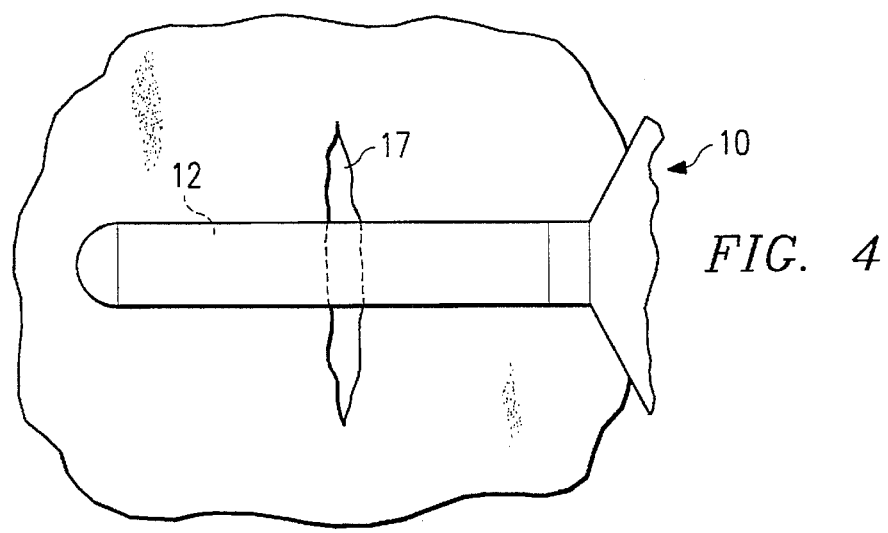
FIG. 4 is a top view of a portion of FIG. 3 showing to closure member disposed over the incision.

After removing the bottom protective member 24, the left end of the closure member 12 (As oriented in the drawing) is pressed onto the skin of the patient adjacent to the wound 17 as shown in FIG. 3. The adhesive layer 16 is in contact with the skin sticking the closure member 12 to the skin adjacent to the left side of the wound 17 as shown in FIGS. 3 and 4. The wound 17 is open at this time.

There is no adhesive on the bottom side of the enlarged viewing member 18 so that the viewing member can be grasped in the fingers of the person applying the device 10 without the device sticking to the user. The user holds the closure member 12 out of contact with the skin on the right side of the wound 17 and exerts a force on the skin on the left side of the wound 17 by pulling to the right on the viewing member 18. The user then pushes on the skin on the right side of the wound 17 toward the skin on the left side of the wound 17 until the edges or sides of the wound 17 are in juxtaposition with the wound 17 closed.

Figure 5:
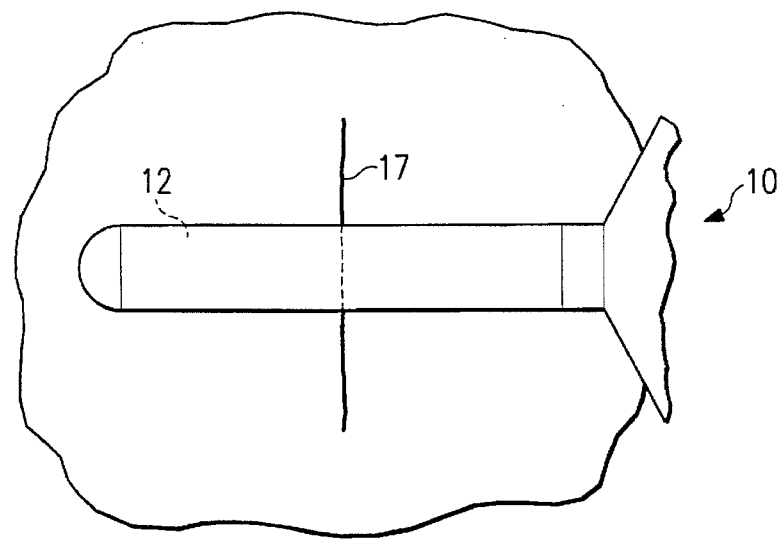
FIG. 5 is a view similar to FIG. 4, but showing the incision closed.
Figure 6:
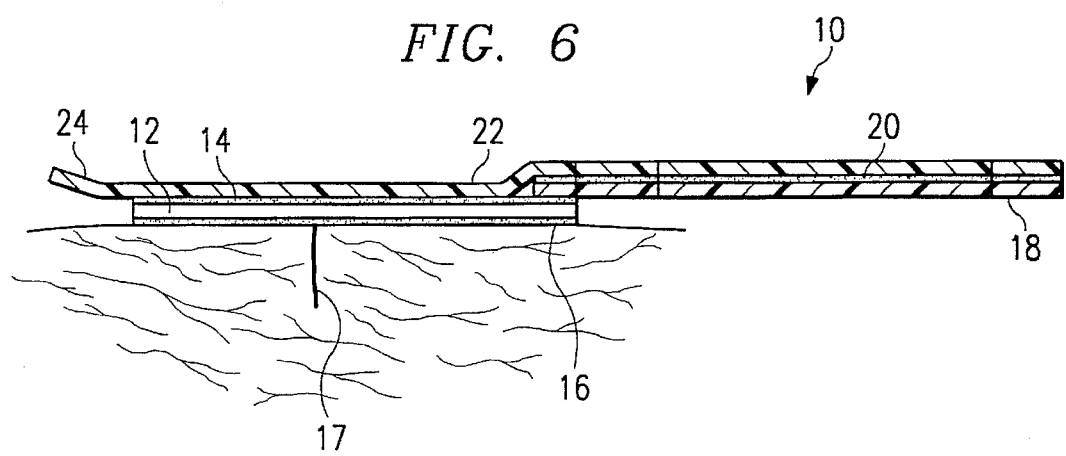
FIG. 6 is a view similar to FIG. 3, but showing the incision closed and having the top protective member removed also.

When this has been accomplished, the closure member 12 is pressed against the skin on the right side of the wound 17 placing the adhesive layer 16 in contact with the skin on the right side of the wound 17. The adhesive layer 16 sticks the closure member 12 to the skin and holds the wound 17 in the closed condition as shown in FIGS. 5 and 6.

It is important to note that during this process, the ends of the wound 17 are visible to the person applying the device 10 on both sides of the closure member 12 even if the closure member is not constructed from a transparent material. Such visibility enables the user to more efficiently and effectively apply the device 10 to place the wound 17 in the closed condition.

The offset end or tab portion 24 on the top protective member 22 is grasped and a pull exerted thereon separating the protective member 22 from the closure member 12 and the viewing member 18, exposing the adhesive layer 14 on the closure member 12 and the adhesive layer 20 on the viewing member 18. The member 22 can be easily grasped by a user wearing gloves due to the configuration of the end 24 on the closure member 12 and the member 22 can be separated easily from the viewing member 18 due to the release coating on the member 22.

Figure 7:
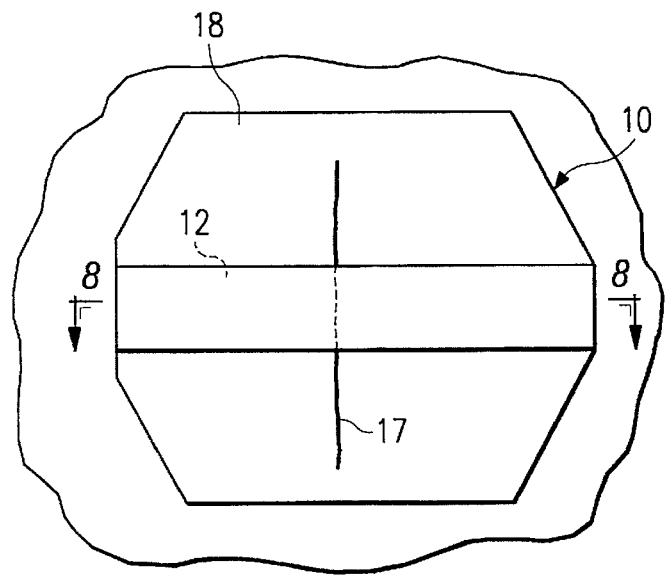
FIG. 7 is a view similar to FIG. 5, but showing the viewing member folded over the closure member and encompassing the incision in the skin.
Figure 8:
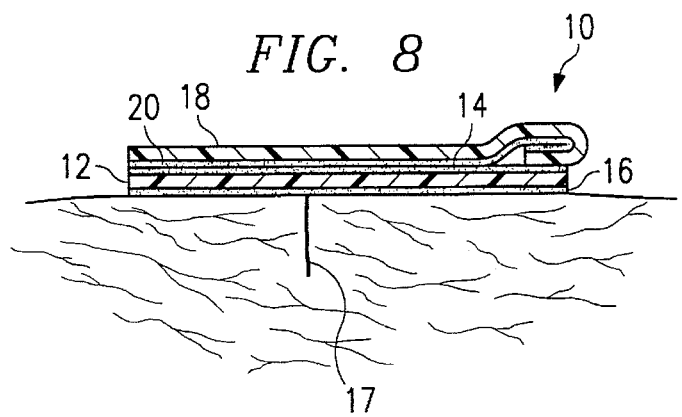
FIG. 8 is a view taken generally along the line 8—8 of FIG. 7.

When the protective member 22 has been removed, the user continues to pull the viewing member 18 over the closure member 12 and over the wound 17 as shown in FIGS. 7 and 8. The adhesive layer 20 on the viewing member 18 sticks the member 18 to the patient's skin enclosing the wound 17 to aid in maintaining the sterility of the wound. The wound can still be viewed since the viewing member 18 is constructed from a transparent material. The viewing member 18 is further adhered to the closure member 12 due to the adhesive layer 14 on the closure member 12.

Figure 9:
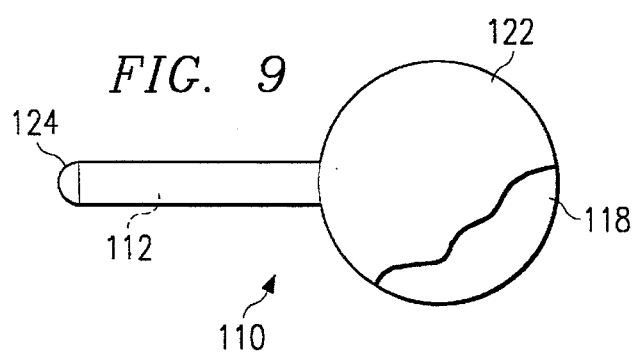
FIG. 9 is a plan view of a modified form of incision closing device that is also constructed in accordance with the teachings of the invention.

Referring to FIG. 9, a modified form of a closure device that is also constructed in accordance with the invention is indicated generally by the reference character 110. Although all the components are not shown in FIG. 9, the wound or incision closure device 110 includes the same structural components as did the device 10 which was described in detail hereinbefore. As shown in FIG. 9, the device 110 includes a relatively narrow closure member 112, an enlarged top protective member 122, and an enlarged viewing member 118. (The protective member 122 is partially cut away to show the viewing member 118.)

The modification of FIG. 9, as compared to the closure device 10, resides in the change to the configuration of the viewing member 118. While the viewing member 18 has a generally hexagonal shape, the viewing member 118 is generally circular. The closure device 110 is used in the same manner as previously described in detail with respect to the closure device 10.

Figure 10:
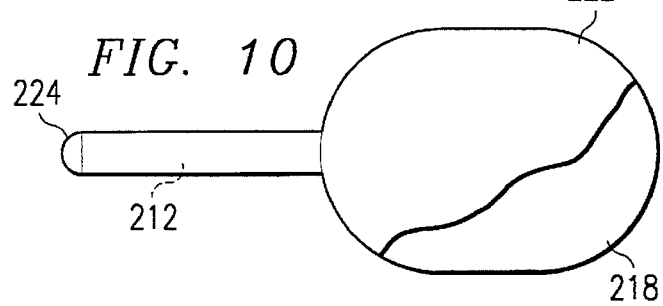
FIG. 10 is a plan view of another modified form of incision closing device that is also constructed in accordance with the teachings of the invention.

Referring to FIG. 10, a modified form of closure device that is also constructed in accordance with the invention is indicated generally by the reference character 210. Although all the components are not shown in FIG. 10, the device 210 includes the same structural components as did the device 10 which was described in detail hereinbefore. As shown in FIG. 10, the wound or incision closure device 210 includes a relatively narrow closure member 212, an enlarged top protective member 222, and an enlarged viewing member 218. (The member 222 is partially cut away to show the viewing member 218.)

The modification of FIG. 10 resides in the change to the configuration of the viewing member 218 as compared to the viewing member 18 of the closure device 10. While the viewing member 18 has a generally hexagonal shape and the viewing member 118 has a generally circular shape, the viewing member 218 is generally elliptical. The closure device 210 is used in the same manner as previously described in detail with respect to the closure device 10.

The various configurations of the closure devices 10, 110, and 210 illustrate that the present invention allows varying the configuration the viewing member as desired for specific applications while still providing a sufficiently large tab portion to be easily grasped by a person wearing surgical gloves while applying the device to close the wound. The viewing member is preferably large enough to completely enclose the wound to aid in preventing infection by sealing the area around the wound to maintain the sterility of the wound.

It will be appreciated from the foregoing detailed description that a device constructed in accordance with the invention provides a closure device that is not only effective to close a wound or the like, but one that can be easily used by a person wearing surgical gloves because of the arrangement of the bent or offset ends of the protective members.

Further, a closure device constructed in accordance with the invention is simple to use and because of its unitary construction is not susceptible to having components thereof lost while applying the device rendering it ineffective or totally unusable. This feature of the invention results from the use of adhesives to assemble the various components of the device into the unitary structure received by the user when the closure device is removed from its packaging (not shown) for use.

Although the present invention and its advantages have been described in detail, it should be understood that various changes, substitutions, and alterations can be made therein without departing from the spirit and scope of the invention as defined in the following claims.

What is claimed is:

1. An incision closure device providing visibility of an incision during closure and permitting full observation of the incision after the closure device has been applied, comprising:

an elongated closure member having a width substantially narrow as compared to the length of the incision to be closed;

an adhesive on a side thereof arranged to be applied to skin adjacent to the incision for holding adjacent edges of the incision closed;

an enlarged, substantially transparent, viewing member having one end attached to an adjacent end of the closure member, the viewing member having a length at least equal to the length of the closure member and having a width greater than the width of the closure member; and, an adhesive on a side of the viewing member remote from the closure member for securing the viewing member to the skin adjacent to the incision when the viewing member is disposed in overlying relation to the closure member.

2. The closure device of claim 1 wherein the width of the viewing member is at least twice the width of the closure member.

3. The closure device of claim 2 wherein the closure member and viewing member are connected by an adhesive.

4. The closure device of claim 1 wherein the closure member and viewing member are connected by an adhesive.

5. An incision closure device providing visibility of an incision during closure and permitting full observation of the incision after the closure device has been applied, comprising:

an elongated closure member having a width substantially narrow as compared to the length of the incision to be closed;

an adhesive on a side thereof arranged to be applied to skin adjacent to the incision for holding adjacent edges of the incision closed;

an enlarged, substantially transparent, viewing member having one end attached to an adjacent end of the closure member, the viewing member having a length at least equal to the length of the closure member and having a width greater than the width of the closure member; and, an adhesive on a side of the viewing member remote from the closure member for securing the viewing member to the skin adjacent to the incision when the viewing member is disposed in overlying relation to the closure member; and also including an adhesive located on the side of the closure member adjacent to the viewing member.

6. The closure device of claim 5 and also including a protective member releasably connected to the side of the closure member to be adhered to the skin, the protective member being at least coextensive with the closure and viewing members and having a release coating thereon so that the protective member can be readily removed from the closure member when the device is to be applied to an incision.

7. The closure device of claim 6 and also including a second protective member releasably connected to the side of the viewing member to be adhered to the skin, the second protective member being constructed from a substantially transparent material and being at least coextensive with the closure and viewing members and having a release coating thereon so that the protective member can be readily removed from the viewing member when the device is to be applied to an incision.

8. The closure device of claim 7 and also including a tab portion formed on the first mentioned protective member projecting at an angle away from the viewing member to facilitate the removal of the first mentioned protective member from the viewing and closure members by a user wearing surgical gloves.

9. The closure device of claim 8 and also including a tab portion formed on the second protective member projecting at an angle away from the closure member to facilitate the removal of the protective member from the viewing and closure members by a user wearing surgical gloves.

10. The closure device of claim 9 wherein the width of the viewing member is at least twice the width of the closure member.

11. The closure device of claim 9 wherein the closure member and viewing member are connected by an adhesive.

12. The closure device of claim 7 and also including a tab portion formed on the second protective member projecting at an angle away from the closure member to facilitate the removal of the protective member from the viewing and closure members by a user wearing surgical gloves.

13. The closure device of claim 6 and also including a tab portion formed on the protective member projecting at an angle away from the viewing member to facilitate the removal of the protective member from the viewing and closure members by a user wearing surgical gloves.

14. The closure device of claim 6 wherein the closure member and viewing member are connected by an adhesive.

15. The closure device of claim 6 wherein the width of the viewing member is at least twice the width of the closure member.

16. The closure device of claim 15 wherein the closure member and viewing member are connected by an adhesive.

17. A wound closure device providing visibility of an incision during closure and permitting full observation of the incision after the closure device has been applied, comprising:

an elongated closure member having a width substantially narrow as compared to the length of the incision to be closed;

an adhesive on a side thereof arranged to be applied to skin adjacent to the incision for holding adjacent edges of the incision closed;

an enlarged, substantially transparent, viewing member having one end attached to an adjacent end of the closure member, the viewing member having a length at least equal to the length of the closure member and having a width greater than the width of the closure member;

an adhesive on a side of the viewing member remote from the closure member for securing the viewing member to the skin adjacent to the incision when the viewing member is disposed in overlying relation to the closure member; and the closure member and viewing member are connected by an adhesive.

18. A wound closure device providing visibility of an incision during closure and permitting full observation of the incision after the closure device has been applied, comprising:

an elongated closure member having a width substantially narrow as compared to the length of the incision to be closed;

an adhesive on a side thereof arranged to be applied to skin adjacent to the incision for holding adjacent edges of the incision closed;

an enlarged, substantially transparent, viewing member having one end attached to an adjacent end of the closure member, the viewing member having a length at least equal to the length of the closure member and having a width greater than the width of the closure member;

an adhesive on a side of the viewing member remote from the closure member for securing the viewing member to the skin adjacent to the incision when the viewing member is disposed in overlying relation to the closure member;

the closure member and viewing member are connected by an adhesive;

a second protective member releasably connected to the side of the viewing member to be adhered to the skin, the second protective member being constructed from a substantially transparent material and being at least coextensive with the closure and viewing members and having a release coating thereon so that the protective member can be readily removed from the viewing member when the device is to be applied to an incision; and a tab portion formed on the first mentioned protective member projecting at an angle away from the viewing member to facilitate the removal of the first mentioned protective member from the viewing and closure members by a user wearing surgical gloves.

* * * * *